United States Patent [19]
Outtrup et al.

[11] Patent Number: 5,928,929
[45] Date of Patent: Jul. 27, 1999

[54] ALKALINE PROTEASE FROM *BACILLUS SP.*I612

[75] Inventors: Helle Outtrup; Lars Sparre Conrad, both of Bagsvaerd, Denmark

[73] Assignee: Novo Nordisk A/S, Bagsvaerd, Denmark

[21] Appl. No.: 08/887,383

[22] Filed: Jul. 2, 1997

Related U.S. Application Data

[63] Continuation of application No. PCT/DK96/00061, Feb. 8, 1996.

[30] Foreign Application Priority Data

Feb. 10, 1995 [DK] Denmark ................................. 0157/95
Mar. 17, 1995 [DK] Denmark ................................. 0274/95

[51] Int. Cl.$^6$ ............................. C12N 9/54; C11D 3/386; C11D 7/42
[52] U.S. Cl. ......................... 435/221; 510/320; 510/392; 510/530
[58] Field of Search ............................. 435/221; 510/392, 510/114, 320, 530

[56] References Cited

U.S. PATENT DOCUMENTS 3,875,006  4/1975  Belloc et al. ............................ 435/220
4,480,037  10/1984  Ichishima et al. ....................... 435/221

FOREIGN PATENT DOCUMENTS 63-192387  8/1988  Japan .
88/03947   6/1988  WIPO .
88/03948   6/1988  WIPO .
9207067    4/1992  WIPO .
9401532    1/1994  WIPO .
9507350    3/1995  WIPO .
96/24666   8/1996  WIPO .

OTHER PUBLICATIONS

Tsuchida et al. (1986) Curr. Microbiol. 14(1), "An alkaline proteinase of an alkalophilic *Bacillus sp*", pp. 7–12, in Chem. Abst. (1987) 106, Abstr. No. 29140.

Epremyan et al. (1981) Biokhimiya, 46 (5), "Extracellular Serine Proteinase from *Bacillus–thuringiensis*", pp. 920–929, in Biosis An 83:178818.

*Primary Examiner*—Jon P. Weber
*Attorney, Agent, or Firm*—Steve T. Zelson, Esq.; Valeta Gregg, Esq.

[57] ABSTRACT

This invention is in the field of detergent proteases obtainable from strains of a new Bacillus sp. I 612. Moreover, the invention is directed towards a process for the preparation of the protease, the use of the protease as a detergent enzyme, and detergent compositions comprising the protease of the invention.

11 Claims, 2 Drawing Sheets

5,928,929

ALKALINE PROTEASE FROM *BACILLUS SP.* I612

CROSS-REFERENCE TO RELATED APPLICATIONS

This application is a continuation application of Ser. No. PCT/DK96/00061 filed Feb. 8, 1996 and claims priority under 35 U.S.C. 119 of Danish application Ser. Nos. 0157/95 and 0274/95 filed Feb. 10, 1995 and Mar. 17, 1995, respectively, the contents of which are fully incorporated herein by reference.

FIELD OF INVENTION

The present invention relates to detergent proteases obtainable from strains of Bacillus sp. More specifically, the invention is directed towards a novel alkaline protease derived from a strain of Bacillus sp. I 612. Moreover, the invention is directed towards a process for the preparation of the protease, the use of the protease as a detergent enzyme, and detergent compositions comprising the protease of the invention.

BACKGROUND OF THE INVENTION

Detergent enzymes have been marketed for more than 20 years and are now well established as normal detergent ingredients in both powder and liquid detergents all over the world.

Enzymes used in washing formulations comprise many different enzymes such as proteases, lipases, amylases, cellulases, as well as other enzymes, or mixtures thereof. Commercially the most important enzymes are the proteases.

Detergent proteases have been developed by isolation of proteases found in nature followed by testing in detergent formulations. Most detergent proteases are obtained from members of the genus Bacillus.

Examples of commercial protease products are ALCALASE™, ESPERASE™ and SAVINASE™, all supplied by Novo Nordisk A/S, Denmark. The ALCALASE™ protease is produced by strains of the species *Bacillus licheniformis*. The ESPERASE™ and SAVINASE™ proteases are obtained by cultivation of strains of alkalophilic Bacilli.

The washing traditions, especially the used washing temperature, the hardness of the used water, and the ingredients of the detergents vary very much from one country to another. Typical conditions are outlined below:

low pH and low water hardness: liquid detergents in US and Asia;

low pH and high water hardness: liquid detergents in Europe;

high pH and low water hardness: powder detergents in US and Asia; and high pH and high water hardness: powder detergents in Europe.

(A low pH in detergents is typically a pH in the range 8.0–9.5, in particular around 9; a high pH in detergents is typically a pH in the range 10–11.5, in particular around 10.5. A low water hardness is typically in the range 3–6° dH; a high water hardness is typically in the range 15–20° dH, in particular around 18° dH).

Furthermore, the compositions of the detergents are changing these years in order to make the washing process more environmental friendly. All these differences and changes within the detergent industry make the field extremely complicated. There is therefore a need all the time to find new proteases which perform optimally at a certain specified set of conditions.

SUMMARY OF THE INVENTION

It is an object of the present invention to provide novel detergent proteases with improved washing performance at moderate to low wash temperatures.

Accordingly, in its first aspect, the invention provides a protease having immunochemical properties identical or partially identical to those of a protease derived from the strain Bacillus sp. I 612, DSM 9701.

In a second aspect, the invention relates to an isolated biologically pure culture of a strain of Bacillus sp. represented by the strain Bacillus sp. I 612. In a more specific aspect, the invention relates to a strain of Bacillus sp. I 612, DSM 9701, or a mutant or a variant thereof.

In a third aspect, the invention provides a process for the preparation of the protease, which process comprises cultivation of a protease producing strain of Bacillus sp. I 612 in a suitable nutrient medium, containing carbon and nitrogen sources and inorganic salts, followed by recovery of the desired enzyme. In a more specific aspect, Bacillus sp. I 612, DSM 9701, or a mutant or a variant thereof, or another host organism carrying the gene encoding a protease having immunochemical properties identical or partially identical to those of the protease derived from Bacillus sp. I 612 is cultivated.

In a fourth aspect, the use of the enzyme as a detergent enzyme is claimed. In more specific aspects, the invention provides detergent compositions and detergent additives comprising the protease.

In a fifth aspect, the invention provides a washing process comprising addition of the protease.

BRIEF DESCRIPTION OF DRAWINGS

The present invention is further illustrated by reference to the accompanying drawings, in which.

DETAILED DISCLOSURE OF THE INVENTION

The Microorganism

Figure 1:
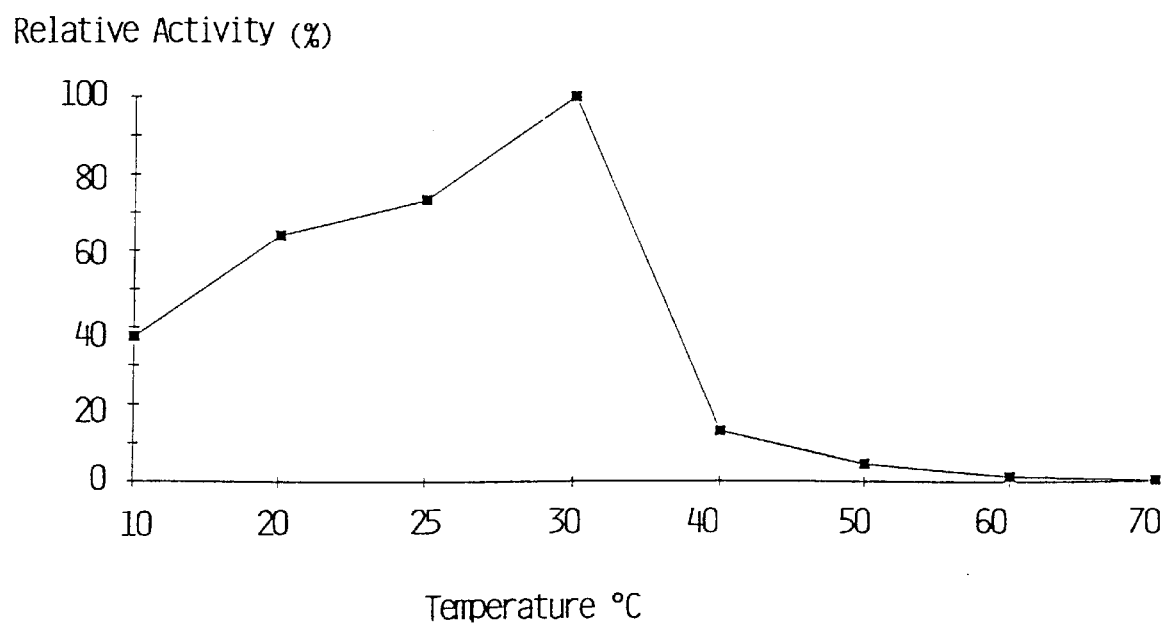
FIG. 1 shows the relation between temperature and the proteolytic activity of an enzyme according to the invention (the enzyme preparation obtained according to Ex. 1, with 1% of casein as substrate and at pH 9.5)

The novel microorganism of the invention, able to produce an enzyme of the invention, is represented by the strain that was isolated from a sample of soil. Bacillus sp. I 612 has been deposited according to the Budapest Treaty on the International Recognition of the Deposits of Microorganisms for the Purpose of Patent Procedures, on Jan. 30, 1995 at Deutsche Sammlung von Mikroorganismen und Zellkulturen GmbH (DSM), Mascheroder Weg 1b, D-38124 Braunschweig, Federal Republic of Germany under Accession No. DSM 9701.

The microorganism of this invention is an aerobic, spore forming bacterium belonging to the genus Bacillus. Morphologically it can be described as motile rods with a diameter of 0.8–1.0 micron, and a length of 2–5 micron. The spores are cylindrical to ellipsoid, not swelling the sporangium, central to subterminal. Optimum temperature for growth is within 25–35° C., and optimal pH for growth is within 7–9.5, with weak growth at pH 10.

Cultivation of the Microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea, and albumin. In addition, the nutrient medium should also contain usual trace substances.

The novel Bacillus species of this invention have, for growth, a neutral pH-optimum. Therefore, the cultivation is preferably conducted at pH 7–9. For cultivation in tank fermentors it is necessary to use artificial aeration. The rate of aeration is similar to that used in conventional tank fermentation.

After fermentation, liquid enzyme concentrates may be produced by removal of coarse material from the broth or, if desired, concentration of the broth by, e.g., evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone. Removal of the water in the broth by suitable drying methods, such as spray-drying, may also be employed.

Assay for Proteolytic Activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5). A folder AF 228, describing the analytical method, is available upon request to Novo Nordisk A/S, Denmark, which folder is hereby included by reference.

The Enzyme

The enzyme of the invention is a novel detergent protease. It is obtainable by cultivation of a microorganism of the invention, preferably Bacillus sp. I 612, DSM 9701, or a mutant or a variant thereof, in a suitable nutrient medium, containing carbon and nitrogen sources and inorganic salts. The enzyme can also be obtained by recombinant DNA-technology.

The protease of the invention may be characterized by the physical-chemical properties described below.

Physical-Chemical Properties

A molecular weight of 31 kD, determined by SDS-PAGE. A pI at about 8.0 could be determined by isoelectric focusing on LKB Ampholine® PAG plates. The protease activity is inhibited by PMSF, α-1-antitrypsin, and EDTA. Soybean-protein inhibitor does not influence the protease activity.

The found result that the protease of the invention is inhibited by both PMSF and by EDTA is very surprising; an inhibition by PMSF shows that the protease is a serine protease, but normally serine proteases tolerate EDTA, and furthermore, it is very extraordinary that the protease of the invention is inhibited by EDTA and at the same time is a very good wash-performer as shown in Example 2.

The temperature activity relationship was determined with 1% of casein as substrate and at pH 9.5. The assay for proteolytic activity described previously was used with the modification that the incubation temperature was varied in the interval of from 10° to 70° C.

The result is shown in FIG. 1. It appears from the figure that the enzyme possesses proteolytic activity from temperatures below 10° C. to about 40° C., and has a temperature optimum at around 30° C. It can be seen from FIG. 1 that the protease has less than 20% activity at 40° C.

The dependence of activity on pH was determined by the same procedure using buffers adjusted to predetermined pH values in the pH range of from 6 to 11.

Figure 2:
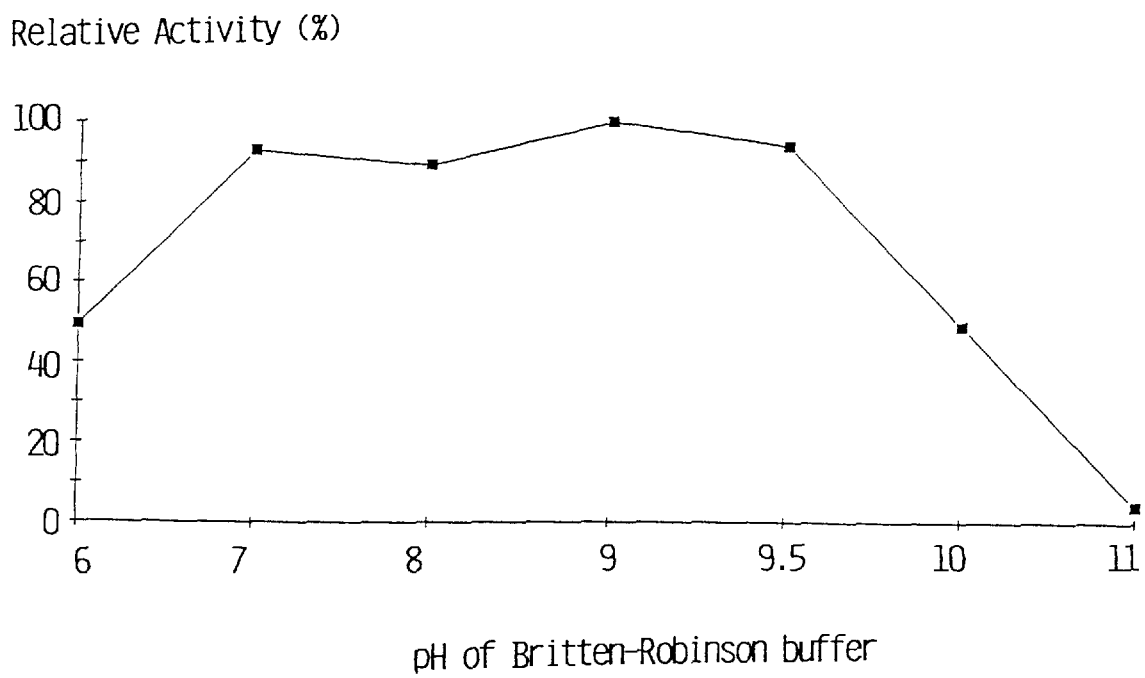
FIG. 2 shows the relation between pH and the proteolytic activity of an enzyme according to the invention (the enzyme preparation obtained according to Ex. 1, with 1% of casein as substrate and at 25° C.).

The result is shown in FIG. 2. It appears from this figure that the enzyme possesses proteolytic activity at pH values below 6 to about 10, with a pH optimum in the range of from pH 7 to pH 9.5.

The protease of the invention possesses especial potentials in detergents with medium ionic strength and medium pH and moderate to low wash temperatures.

Immunochemical Properties

The protease of the invention has immunochemical properties identical or partially identical (i.e. at least partially identical) to those of a protease derived from the strain Bacillus sp. I 612, DSM 9701.

The immunochemical properties for various Bacillus proteases are indeed a very distinguishing feature: whereas pH-optimum, temperature-optimum, pI etc. as disclosed above are more or less the same, different immunochemical properties result in very different stability in various detergents.

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen; *Handbook of Immunoprecipitation-in-Gel Techniques;* Blackwell Scientific Publications (1983), chapters 5 and 14. The terms "antigenic identity" and "partial antigenic identity" are described in the same book, chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Using the ouchterlony double immunodiffusion test described above the protease of the invention showed no cross reaction to the known serine proteases:

ALCALASE™ (available from Novo Nordisk A/S)
SAVINASE™ (available from Novo Nordisk A/S)
ESPERASE™ (available from Novo Nordisk A/S)

subtilisin Novo (available from Novo Nordisk A/S), KAZUSASE™ (available from SHOWA DENKO), the Bacillus proteases described in WO 92/07067, the Bacillus proteases described in WO 92/17576, the Bacillus proteases described in WO 92/17577, the Bacillus proteases described in WO 92/17578, the Bacillus proteases described in WO 93/18140, the Bacillus proteases described in WO 93/24623, the Bacillus proteases described in WO 94/01532, and the Bacillus proteases described in WO 95/07350.

Various Bacillus proteases tolerate various detergents with a great variety, and one of the best tools today in differentiating between Bacillus proteases is the immunochemical identity tool.

Detergent Compositions

According to the invention, the protease may typically be a component of a detergent composition, e.g., a dishwashing or a laundry detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, lipase, cutinase, cellulase, peroxidase, and oxidase, e.g., laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1-2 EO) or alkyl sulfate (e.g., $C_{16-18}$) | 1–4% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O$, $2SiO_2$) | 2–6% |
| Zeolite (as NaAlSiO$_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1-2 EO) or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $Na_2CO_3$) | 15–21% |
| Soluble silicate (as $Na_2O$, $2SiO_2$) | 1–4% |
| Zeolite (as NaAlSiO$_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as $Na_2SO4$) | 0–4% |
| Sodium perborate (as $NaBO_3.H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO, or $C_{12-15}$ alcohol, 5 EO) | 3–9% |
| Soap as fatty acid (e.g., oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g., PVP, maleic/acrylic acid copolymer, PEG) | 1–5% |
| Enzymes (calculated as pure enzyme protein) | 0.0001–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2-3 EO) | 8–15% |
| Alcohol ethoxylate (e.g., $C_{12-15}$ alcohol, 7 EO, or $C_{12-15}$ alcohol, 5 EO) | 3–9% |
| Soap as fatty acid (e.g., lauric acid) | 0–3% |
| Aminoethanol | 1–5% |
| Sodium citrate | 5–10% |
| Hydrotrope (e.g., sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent compositions as described in compositions 1–12 wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$—$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g., SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g., polycarboxylates and PVP) | 0–5% |
| Enzymes (calculated as pure enzyme protein) | 0.0001–0.1% |
| Minor ingredients (e.g., optical brightener, photo bleach, perfume, suds suppressors) | 0–5% |

15) A detergent composition formulated as a granulate having a bulk density of at least 600 g/l comprising

| | |
|---|---|
| ($C_{12}$—$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The protease of the invention may be incorporated in concentrations conventionally employed in detergents. It is at present contemplated that, in the detergent composition of the invention, the protease may be added in an amount corresponding to 0.00001–1 mg (calculated as pure enzyme protein) of protease per liter of wash liquor.

The invention is further illustrated in the following examples, which are not intended to be in any way limiting to the scope of the invention as claimed.

EXAMPLE 1

Bacillus sp. I 612, DSM 9701, was cultivated at 30° C. on a rotary shaking table (300 r.p.m.) in 500 ml baffled Erlenmeyer flasks containing 100 ml of medium of the following composition (per liter):

| | | |
|---|---|---|
| Potato starch | 100 | g |
| Ground barley | 50 | g |
| Soybean flour | 20 | g |
| $Na_2HPO_4 \times 12 H_2$ | 9 | g |
| Pluronic ® | 0.1 | g |
| Sodium caseinate | 10 | g |

The starch in the medium is liquified with α-amylase, and the medium is sterilized by heating at 120° C. for 45 minutes.

After sterilization the pH of the medium is adjusted to 9.0 by addition of 10 ml of a 1 M solution of sodium bicarbonate.

After cultivation (3 days), and after separation of the solid material the protease was purified by a conventional chromatographic method.

Yield from 2.5 l of culture broth was 50 ml with 45 CPU/l. Purity was more than 90% as judged by SDS-PAGE.

The characteristics of the preparation prepared in accordance with this Example have been referred to earlier in this specification, and reference is made hereto.

EXAMPLE 2

Wash Performance of Bacillus sp. I 612 protease (at 25° C.)

The wash performance tests were accomplished on grass juice soiled cotton, in a model wash system at 25° C., at a constant temperature for 10 minutes.

The tests were performed at protease concentrations of 1, 2, 7.5, 20, and 50 nM.

2.0 g/l of an American type powder detergent composition were used in the test. The detergent did not contain any enzymes prior to the addition of the protease of the invention. The detergent was dissolved in approx. 6° dH (German Hardness) water. The pH of the wash liquor was 10. The textile/wash liquor ratio was approximately 5 g of textile per liter of wash liquor. For each enzyme concentration two independent tests were performed.

Subsequent to the fabric washing, the cloths were flushed in running tap water for 20 minutes and then air-dried. The performance of the protease of the invention and of Savinase™ was assessed by the change ($\Delta R$) of the remission (% R) at 460 nm measured on a Datacolor Elrephometer 2000, $\Delta R$ being the remission after wash with protease added, minus the remission after wash with no protease added.

The results of these tests are shown in Table 1 below (mean of 2 tests).

TABLE 1

| Protease Concentration | $\Delta R$ | |
|---|---|---|
| (nM) | I 612 | SAVINASE ™ |
| 1 | 1.9 | 1.7 |
| 2 | 4.2 | 2.4 |
| 7.5 | 9.1 | 5.5 |
| 20 | 14.4 | 11.1 |
| 50 | 17.8 | 14.3 |

It can be seen from Table 1 that $\Delta R$ (Bacillus sp. I 612) is higher than $\Delta R$ (Savinase™) at all the measured protease concentrations, i.e. the protease of the invention has a better wash performance at all the measured concentrations at 25° C.

EXAMPLE 3

Wash Performance of Bacillus sp. I 612 protease (at 15° C.)

The wash performance tests were accomplished on grass juice soiled cotton, in a model wash system at 15° C., at a constant temperature for 10 minutes.

The tests were performed at protease concentrations of 2, 7.5, 20, and 50 nM.

2.0 g/l of a detergent with the following composition

| Linear alkylbenzenesulfonate | 0.3 | g/l |
| Alcohol ethoxylate | 0.04 | g/l |
| Soap | 0.1 | g/l |
| $Na_2SO_4$ | 0.3 | g/l |
| $Na_2CO_3$ | 0.4 | g/l |
| Zeolith | 0.6 | g/l |
| $Na_3$-citrate | 0.08 | g/l |
| Carboxymethylcellulose | 0.006 | g/l |
| Polycarboxylate | 0.083 | g/l | were used in the test. The detergent was dissolved in approx. 6° dH (German Hardness) water. The pH of the wash liquor was adjusted to pH 10. The textile/wash liquor ratio was approximately 5 g of textile per liter of wash liquor. For each enzyme concentration two independent tests were performed.

Subsequent to the fabric washing, the cloths were flushed in running tap water for 20 minutes and then air-dried. The performance of the protease of the invention and of Savinase™ was assessed by the change ($\Delta R$) of the remission (% R) at 460 nm measured on a Datacolor Elrephometer 2000, $\Delta R$ being the remission after wash with protease added, minus the remission after wash with no protease added.

The results of these tests are shown in Table 2 below (mean of 2 tests).

TABLE 2

| Protease Concentration | $\Delta R$ | |
|---|---|---|
| (nM) | I 612 | SAVINASE ™ |
| 2 | 2.5 | 2.3 |
| 7.5 | 6.6 | 3.9 |
| 20 | 10.5 | 7.9 |
| 50 | 14.5 | 11.8 |

It can be seen from Table 2 that $\Delta R$ (Bacillus sp. I 612) is higher than $\Delta R$ (Savinase™) at all the measured protease concentrations, i.e. the protease of the invention has a better wash performance at all the measured concentrations at 15° C.

We claim:

1. An isolated protease obtainable from Bacillus sp. I 612 having (a) an apparent molecular weight of 31 kD as determined by SDS-PAGE;

(b) a pI at about 8.0;

(c) a pH optimum in the range of from pH 7 to pH 9.5 at 25° C. with casein as substrate;

(d) a temperature optimum at about 30° C. and less than 20% activity at 40° C. at pH 9.5 with casein as substrate; and (e) protease activity inhibited by PMSF and EDTA.

2. The protease of claim 1, which is obtained from the strain Bacillus sp. I 612, DSM 9701.

3. An isolated protease having immunochemical properties identical to those of the protease of claim 2.

4. A process for producing the protease of claim 1, comprising:

(a) cultivating a Bacillus sp. strain in a suitable nutrient medium containing carbon and nitrogen sources and inorganic salts; and (b) recovering the protease.

5. The process of claim 4, wherein the Bacillus sp. strain is Bacillus sp. I 612, DSM 9701.

6. The process of claim 4, wherein the Bacillus sp. strain is a recombinant host strain containing the gene encoding the protease.

7. A detergent composition comprising a surfactant and the protease of claim 1.

8. The detergent composition of claim 7, which further comprises one or more other enzymes.

9. The detergent composition of claim 8, wherein the one or more other enzymes is selected from the group consisting of an amylase, a cellulase, a lipase, an oxidase, and a peroxidase.

10. A detergent additive comprising the protease of claim 1 in the form of a non-dusting granulate, a liquid, a slurry, or a protected enzyme.

11. A process for washing a fabric, comprising treating the fabric with a detergent composition comprising the protease of claim 1.

* * * * *